(12) United States Patent
Ghigo et al.

(10) Patent No.: US 7,910,317 B2
(45) Date of Patent: Mar. 22, 2011

(54) USE OF THE SALIVARY PROTEIN CD14 AS AN INDICATOR OF THE LOW RISK TO DEVELOPING DENTAL CARIES

(75) Inventors: Dario Ghigo, Saluzzo (IT); Loredana Bergandi, Caluso (IT)

(73) Assignee: Universita' Degli Studi di Torino, Turin (IT)

( * ) Notice: Subject to any disclaimer, the term of this patent is extended or adjusted under 35 U.S.C. 154(b) by 288 days.

(21) Appl. No.: 11/995,572

(22) PCT Filed: Jul. 17, 2006

(86) PCT No.: PCT/IB2006/052440
§ 371 (c)(1),
(2), (4) Date: Jan. 14, 2008

(87) PCT Pub. No.: WO2007/010474
PCT Pub. Date: Jan. 25, 2007

(65) Prior Publication Data
US 2008/0206796 A1 Aug. 28, 2008

(30) Foreign Application Priority Data
Jul. 15, 2005 (IT) .............................. TO2005A0489

(51) Int. Cl.
*G01N 33/553* (2006.01)
(52) U.S. Cl. .................................. 435/7.1; 4/7.2; 4/7.92
(58) Field of Classification Search .......................... None
See application file for complete search history.

(56) References Cited

U.S. PATENT DOCUMENTS 7,608,684 B2 * 10/2009 Furusako et al. ............. 530/300

OTHER PUBLICATIONS

Bergandi et al (Eur.J.Oral Sci. 2007. 115:93-96).*
Sakurai K et al., "Co-increase of nerve fibers and HLA-DR-and/or factor-XIIIa-expressing dendritic cells in dentinal caries-affected regions of the human dental pulp: An immunohistochemical study", Journal of Dental Research; vol. 78, No. 10, Oct. 1999, pp. 1596-1608, XP009078056.
Ghafouri, Bijar et al., "Mapping of proteins in human saliva using two-dimensional gel electrophoresis and peptide mass fingerprinting.", Proteomics, vol. 3, No. 6, Jun. 2003, pp. 1003-1015, XP009078068.
Uehara et al., Constitutive Expression of a Bacterial Pattern Recognition Receptor, CD14, in Human Salivary Glands and Secretion as a Soluble Form in Saliva, Clinical and Diagnostic Laboratory Immunology, vol. 10, No. 2, Mar. 2003, p. 286-292.

* cited by examiner

*Primary Examiner* — Jennifer E Graser
(74) *Attorney, Agent, or Firm* — Roylance, Abrams, Berdo & Goodman, L.L.P.

(57) ABSTRACT

It is generally accepted that salivary components are important for dental health, but till now no clear correlation has been found between one or more of said components and the onset of dental caries. The present invention relates to an assay method comprising analysing the presence and/or the content of the salivary soluble CD14 protein from a saliva sample of the individual subjected to examination; the absence of said protein from the salivary sample, or its presence in a reduced amount compared to a predetermined threshold value in caries-free individuals, is considered as a marker of susceptibility to developing caries and/or as a diagnostic element for the existence of ongoing carious lesions.

4 Claims, 1 Drawing Sheet

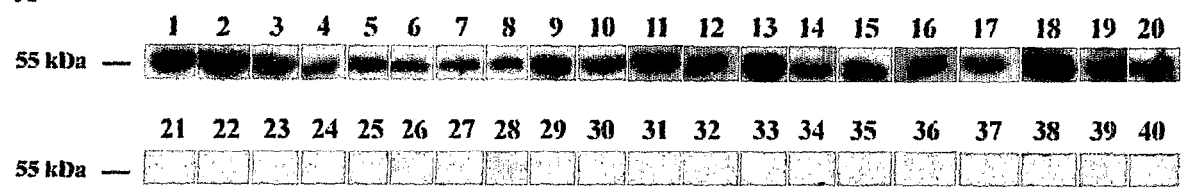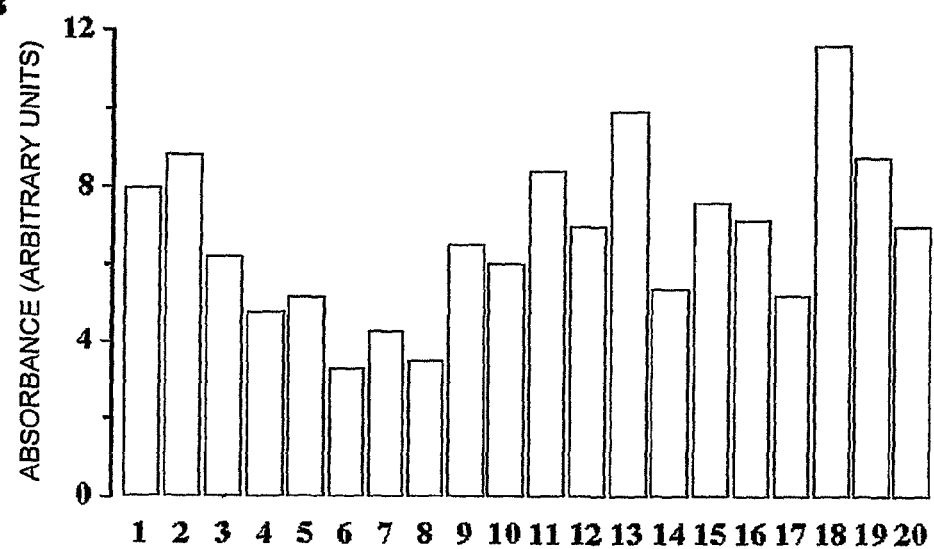

USE OF THE SALIVARY PROTEIN CD14 AS AN INDICATOR OF THE LOW RISK TO DEVELOPING DENTAL CARIES

FIELD OF THE INVENTION

The present invention relates to an in vitro assay method useful for determining the receptivity of an individual to caries, particularly to a method for determining the predisposition of an individual to developing dental caries or for determining the presence of one or more active caries within the oral cavity.

BACKGROUND OF THE INVENTION

Caries is a multifactorial infectious disease, determined by the dynamic balance between pathological factors leading to demineralization and protective factors leading to remineralization (Featherstone, 2004).

Many salivary proteins have been suggested to play a role as either cariogenic or anti-cariogenic factors, depending on their ability to inhibit the growth of acid-producing bacteria, to aggregate them, to promote their adhesion to the tooth surface or to modify the mineralization/demineralization balance (Lenander-Lumikari and Loimaranta, 2000; Nieuw Amerongen et al., 2004).

Understanding the role of salivary proteins in caries development is made more complicated by the fact that many of these proteins are multifunctional (the same protein may perform different functions), redundant (many proteins seem to share the same functions) and amphifunctional (the same protein may have opposite effects, depending on the intraoral environment) (Rudney, 2000; Humphrey and Williamson, 2001).

No significant differences in the protein composition of parotid saliva (Dodds et al., 1997) and whole saliva (Banderas-Tarabay et al., 2002) were detected between caries-active (CA) and caries-free (CF) individuals.

Actually, each band of one-dimensional gel electrophoresis is often composed of different protein types, thus making it difficult to detect quantitative changes in specific proteins. The mapping of human salivary proteins by two-dimensional gel electrophoresis has revealed the presence of many spots which are still to be identified (Ghafouri et al., 2003): one of these proteins could turn out to be primarily involved in the development of caries.

However, the prior art does not contain any indication as to the possible existence of any specific salivary protein which may be used as a marker for the predisposition of an individual to developing caries or as an indicator of the presence of ongoing caries.

SUMMARY OF THE INVENTION

The present invention is based on the recognition of the fact that the expression of the salivary protein sCD14 (soluble CD14) is considerably reduced in the saliva from CA individuals compared to the saliva of CF individuals; in particular, by Western blotting analysis of salivary samples from young CA patients, the sCD14 protein was determined to be absent from all of the salivary samples from young CA patients, whilst it was clearly detectable in the saliva from all of the control age-matched CF individuals.

DETAILED DESCRIPTION OF THE INVENTION

The inverse relationship between the presence of sCD14 in the saliva and the onset of early tooth decay leads to suppose that this salivary protein may play an important role in preventing the development of caries or that its disappearance (or clear-cut reduction) may represent a marker for the presence of active caries.

Thus, the subject-matter of the present invention comprises a prognostic and diagnostic assay method for determining the predisposition of an individual to developing dental caries or for detecting the existence of active caries within the oral cavity, characterized in that it comprises the step of examining a salivary sample from the individual for the presence of the salivary soluble CD14 protein, wherein the absence of said protein from the sample or its presence in a reduced amount compared to a predetermined threshold value in caries-free individuals, is indicative of said predisposition or of the presence of active caries.

CD14 is a 55 kDa membrane glycoprotein expressed predominantly on the surface of monocytes/macrophages and neutrophils, which plays a crucial role in the recognition of several microbial products, such as lipopolysaccharide (LPS, endotoxins) and peptidoglycan, which are major components of Gram-negative and Gram-positive bacteria, respectively, thus participating in the initiation of immune responses (Lien and Ingalls, 2002).

The LPS- or peptidoglycan-CD14 complex, together with other accessory proteins, interacts with cell surface receptors designated as Toll-like receptors, and through the activation of multiple signalling pathways leads to the synthesis of pro-inflammatory cytokines (Guha and Mackman, 2001).

CD14 is expressed on the cell surface via a glycosylphosphatidylinositol anchor, but is also found in a free form in plasma, this being referred to as soluble CD14 (sCD14). sCD14 mediates the activation by LPS of CD14-negative cells, such as endothelial and epithelial cells (Frey et al., 1992).

Major human salivary glands constitutively express and secrete sCD14 into saliva (Sugawara et al., 2002): salivary sCD14 may mediate the activation of CD14-lacking intestinal epithelial cells by LPS via the Toll-like receptor TLR4 (Uehara et al., 2003), and promotes the invasion of oral epithelial cells by Actinobacillus actinomycetemcomitans, thereby increasing the production of interleukin-8 (Takayama et al., 2003). Although this may suggest that human sCD14 could play an important role in the innate immunity in the oral cavity, there is no evidence in the prior art as to a correlation between salivary sCD14 and the receptivity of an individual to caries.

The results obtained within the present invention show that the said protein, besides its multifunctional properties, plays an important role as an anti-cariogenic factor.

A number of hypothesis may be formulated to explain such a function, although the present invention is not intended to be bound nor restricted to any particular explanation of the mechanism of action.

First, sCD14 could enable oral epithelial cells to bind bacteria (thereby preventing their adhesion to the tooth surface) and to produce cytokines capable of recruiting phagocytes at the gingiva-tooth interface (thereby enhancing the clearance of microbes from saliva).

Undoubtedly, CD14-lacking epithelial cells respond to LPS in an sCD14-dependent manner to produce interleukin-8, which induces activation and migration of neutrophils (Uehara et al., 2001).

sCD14 could also modulate the anti-inflammatory properties of saliva, binding with high affinity to human lactoferrin (Baveye et al., 2000), an iron- and LPS-chelating glycoprotein found in exocrine secretions of mammals (Caccavo et al., 2002).

Furthermore, the binding of sCD14 to bacteria could hinder their transition from the planktonic to the sessile phase, retarding plaque formation.

The analysis of the salivary sample for the determination of sCD14 within said sample may be carried out by Western blotting analysis which is known per se; to this end, primary anti-human CD14 antibodies are commercially available, for example the goat polyclonal anti-human CD14 antibody, from Upstate, D.B.A., Italy.

ELISA kits useful for qualitative and quantitative determination of human soluble CD14 are also commercially available.

The following examples illustrate the analyses carried out within the scope of the present invention.

Example 1

Salivary Analysis 40 unrelated Italian healthy children, aged 6 to 12 years, were examined clinically by an experienced dentist; criteria for inclusion were no general diseases, no medication and no extracted teeth. 20 of them (8 males, 12 females; age=8.45+ 0.358 years) were caries-free (CF), and 20 (9 males, 11 females; age=7.9+0.341 years) were caries-active (CA: defined as having from 2 to 8 carious lesions requiring restoration).

The study was approved by the local ethical committee; written and oral informed consent was given by all participants.

The subjects were instructed to refrain from eating, drinking or using breath fresheners for a minimum of 2 hours before collecting saliva. Unstimulated human whole saliva (about 5 ml) was collected between 8 and 10 a.m. by the same examiner prior to clinical examination, to reduce possible circadian variations.

The subjects were invited to clean their teeth with a toothbrush, rinsing the mouth with water. After a 10 min waiting time, subjects were asked to spit out saliva into sterile plastic tubes, which were processed immediately thereafter, to minimize proteins degradation (Banderas-Tarabay et al., 2002).

The samples were supplemented with the protease inhibitor cocktail set III (100 mM AEBSF, 80 µM aprotinin, 5 mM bestatin, 1.5 mM E-64, 2 mM leupeptin, and 1 mM pepstatin; Calbiochem-Novabiochem Corporation, CA) and kept on ice throughout the processing. Saliva was centrifuged at 12,000 rpm for 15 min at 4° C. to remove insoluble material, cells and debris (Ghafouri et al., 2003). 2 ml of the sample were desalted by gel filtration (PD-10 column, Amersham International, Piscataway, N.J.) in 12 mM ammonium bicarbonate, pH 7.1. Eluates were lyophilized and stored at 70° C. until electrophoretic analysis.

Example 2

Western Blot Analysis

Electrophoresis reagents were from Bio-Rad Laboratories (Richmond, Calif.). The protein content of whole saliva was assessed with the BCA kit from Pierce (Rockford, Ill.).

If not otherwise specified, other reagents were purchased from Sigma Chemical Co. (St. Louis, Mo.) and Aldrich (Milan, Italy).

Samples were directly solubilized in lysis buffer (125 mM Tris-HCl, 4% sodium dodecylsulfate, 20% glycerol, pH 6.8, 10% β-mercaptoethanol, and 0.002% bromophenol blue) and boiled for 5 min prior to running gels. Aliquots containing 30 µg of proteins were subjected to sodium dodecylsulfate-polyacrylamide gel electrophoresis (12% polyacrylamide). Proteins were transferred to a PVDF filter membrane (Immobilon P, Millipore, Bedford, Mass.) and incubated with an anti-human CD14 polyclonal antibody (from goat; Upstate, D.B.A., Italy), diluted 1:500 in PBS-BSA 1%.

After overnight incubation, the membrane was washed with PBS-Tween 0.1% and subjected for 1 h to a peroxidase-conjugated anti-goat IgG antibody (from mouse; Amersham International), diluted 1:1000 in PBS-Tween with Blocker Non-Fat Dry Milk 5% (Bio-Rad, Calif.). The PVDF membrane was washed again with PBS-Tween and proteins were detected by enhanced chemiluminescence (Amersham International).

Molecular-weight standards were used in all gels and the density of the protein bands was quantitated with a Gel-Doc densitometer (Bio-Rad).

FIG. 1 illustrates the expression of soluble CD14 in human whole saliva, as determined from the above-illustrated experimental tests: A is the Western blot analysis on saliva samples obtained from the 20 CF subjects (samples 1 to 20) and from the 20 CA subjects (samples 21 to 40); B illustrates the densitometric quantification of the bands obtained from subjects 1-20.

It can be observed that the immunoblot analysis shows the presence of the 55 kDa soluble form of CD14 in all of the CF subjects and its absence from all of the CA subjects.

According to the invention, the absence of sCD14 in a Western blot analysis may be considered as a marker of the predisposition of the individual subjected to examination to developing dental caries or as a diagnostic marker of ongoing caries; furthermore, the determination of a reduced sCD14 expression in the salivary samples compared to a predetermined threshold value in caries-free subjects, is to be considered as predictive of the development of dental caries or as a diagnostic marker of ongoing caries.

For this purpose, the quantitative analysis of sCD14 is preferably carried out by ELISA assay. The determination of the threshold value is preferably carried out by statistical analysis of healthy CF subjects, preferably age-matched with the individual subjected to analysis. In particular, the predictivity of the test is to be considered as particularly high when the value of expression of salivary sCD14 is lower than the 20% of the predetermined threshold value.

The onset of caries in infancy and youth is strongly suggestive of the involvement of genetic factors predisposing to a faster tooth decay. Since several polymorphisms in the 5' flanking region of the CD14 gene have been associated with higher levels of serum sCD14 (Baldini et al., 1999; Vercelli et al., 2001), the reduced salivary expression of sCD14 in young patients with multiple caries is expected to be relatable to a specific polymorphism of the gene.

In that respect, the sCD14 polymorphisms can be studied with the RFLP-PCR technique, which allows to detect every single mutated nucleotide, based on the analysis of the different electrophoretic pattern obtained from the fragment resulting from the cleavage by specific restriction enzymes of the previously PCR-amplified DNA.

Therefore, investigation as to a specific polymorphism of the CD14-encoding gene as a marker of genetic susceptivity to the development of cariesfalls within the scope of the present invention.

REFERENCES

Baldini M, Lohman I C, Halonen M, Erickson R P, Holt P G, Martinez F D (1999). A polymorphism in the 5' flanking region of the CD14 gene is associated with circulating soluble CD14 levels and with total serum immunoglobulin E. *Am J Resp Cell Mol Biol* 20:976-983.

Balekjian A Y, Meyer T S, Montague M E, Longton R W (1976). Electrophoretic patterns of parotid fluid from caries-resistant and caries-susceptible individuals. *J Dent Res* 54:850-856.

Banderas-Tarabay J A, Zacarias-D'Oleire I G, Garduno-Estrada R, Aceves-Luna E, Gonzalez-Begne M (2002). Electrophoretic analysis of whole saliva and prevalence of dental caries. A study in Mexican dental students. *Arch Med Res* 33:499-505.

Baveye S, Elass E, Fernig D G, Blanquart C, Mazurier J, Legrand D (2000). Human lactoferrin interacts with soluble CD14 and inhibits expression of endothelial adhesion molecules, E-selectin and ICAM-1, induced by the CD14-lipopolysaccharide complex. *Infect Immun* 68:6519-6525.

Caccavo D, Pellegrino N M, Altamura M, Rigon A, Amati L, Amoroso A, et al. (2002). Antimicrobial and immunoregulatory functions of lactoferrin and its potential therapeutic application. *J Endotoxin Res* 8:403-417.

Dodds M W, Johnson D A, Mobley C C, Hattaway K M (1997). Parotid saliva protein profiles in caries-free and caries-active adults. *Oral Surg Oral Med Oral Pathol* 83:244-251.

Featherstone J D B (2004). The continuum of dental caries. Evidence for a dynamic disease process. *J Dent Res* 83:C39-C42.

Frey E A, Miller D S, Jahr T G, Sundan A, Bazil V, Espevik T, et al. (1992). Soluble CD14 participates in the response of cells to lipopolysaccharide. *J Exp Med* 176:1665-1671.

Ghafouri B, Tagesson C, Lindahl M (2003). Mapping of proteins in human saliva using two-dimensional gel electrophoresis and peptide mass fingerprinting. *Proteomics* 3:1003-1015.

Guha M, Mackman N (2001). LPS induction of gene expression in human monocytes. *Cell Signal* 13:85-94.

Humphrey S P, Williamson R T (2001). A review of saliva: normal composition, flow, and function. *J Prosthet Dent* 85:162-169.

Lenander-Lumikari M, Loimaranta V (2000). Saliva and dental caries. *Adv Dent Res* 14:40-47.

Lien E, Ingalls R R (2002). Toll-like receptors. *Crit Care Med* 30:S1-S11.

Nieuw Amerongen A V, Bolscher J G, Veerman E C (2004). Salivary proteins: protective and diagnostic value in cariology? *Caries Res* 38:247-253.

Rudney J D (2000) Saliva and dental plaque. *Adv Dent Res* 14:29-39.

Schutt C, Schilling T, Grunwald U, Schonfeld W, Kruger C. (1992). Endotoxin-neutralizing capacity of soluble CD14. *Res Immunol* 143:71-78.

Sugawara S, Uehara A, Tamai R, Takada H (2002). Innate immune responses in oral mucosa. *J Endotoxin Res* 8:465-468.

Takayama A, Satoh A, Ngai T, Nishimura T, Ikawa K, Matsuyama T. et al. (2003). Augmentation of *Actinobacillus actinomycetemcomitans* invasion of human oral epithelial cells and up-regulation of interleukin-8 production by saliva CD14. *Infect Immun* 71:5598-5604.

Uehara A, Sugawara S, Watanabe K, Echigo S, Sato M, Yamaguchi T, et al. (2003). Constitutive expression of a bacterial pattern recognition receptor, CD14, in human salivary glands and secretion as a soluble form in saliva. *Clin Diagn Lab Immunol* 10:286-292.

Uehara A, Sugawara S, Tamai R, Takada H (2001). Contrasting responses of human gingival and colonic epithelial cells to lipopolysaccharide, lipoteichoic acids and peptidoglycans in the presence of soluble CD14. *Med Microbiol Immunol* 189:185-192.

Vercelli D, Baldini M, Stern D, Lohman I C, Halonen M, Martinez F (2001). CD14: a bridge between innate immunity and adaptive IgE responses. *J Endotoxin Res* 7:45-48.

The invention claimed is:

1. A method for diagnosing existence of dental caries in an individual, comprising the steps of: obtaining a salivary sample from the individual; and analysing by Western Blotting or ELISA said salivary sample from the individual to determine the presence or absence of salivary soluble CD14 protein in said salivary sample, wherein absence of said salivary soluble CD14 protein in said salivary sample is indicative of the existence of dental carries in the individual.

2. A method for diagnosing existence of dental caries in an individual, comprising the steps of: obtaining a salivary sample from the individual; analysing by Western Blotting or ELISA said salivary sample from the individual for the presence of salivary soluble CD14 protein in said salivary sample; obtaining a quantitative value of expression of said salivary soluble CD14 protein in said salivary sample; comparing said quantitative value of expression of said salivary soluble CD14 protein in said salivary sample from the individual with a predetermined value of the expression of said salivary soluble CD14 protein obtained from statistical analysis by ELISA of a salivary sample from individuals know to be free of dental carries, wherein a reduced quantitative value of expression of said salivary soluble CD14 protein in said salivary sample from the individual compared with said predetermined value is indicative of the existence of dental carries in the individual.

3. The assay method according to claim 2, wherein the existence of dental caries is determined as positive when said quantitative value of expression of salivary soluble CD14 in said salivary sample subjected to analysis is at least 20% lower than said predetermined quantitative value.

4. A method for diagnosing existence of dental caries in an individual, comprising the steps of: obtaining a salivary sample from the individual; and analysing by Western Blotting or ELISA said salivary sample from the individual to detect the salivary soluble CD14 protein in said salivary sample, wherein non-detection of said salivary soluble CD14 protein in said salivary sample is indicative of the existence of dental carries in the individual.

* * * * *